United States Patent

Kornreich et al.

[11] Patent Number: 5,510,458
[45] Date of Patent: Apr. 23, 1996

[54] CRF ANTAGONISTS

[75] Inventors: Wayne D. Kornreich, San Diego, Calif.; Jean F. Hernandez, Noyarey, France; Jean E. Rivier, La Jolla, Calif.; Catherine L. Rivier, La Jolla, Calif.; Wylie W. Vale, Jr., La Jolla, Calif.

[73] Assignee: The Salk Institute For Biological Studies, La Jolla, Calif.

[21] Appl. No.: 162,178

[22] PCT Filed: Jun. 12, 1992

[86] PCT No.: PCT/US92/05101

§ 371 Date: Dec. 14, 1993

§ 102(e) Date: Dec. 14, 1993

[87] PCT Pub. No.: WO92/22576

PCT Pub. Date: Dec. 23, 1992

Related U.S. Application Data

[63] Continuation-in-part of Ser. No. 715,752, Jun. 14, 1991, Pat. No. 5,245,009.

[51] Int. Cl.⁶ .................................................. C07K 14/695
[52] U.S. Cl. ...................... 530/306; 530/324; 530/325; 930/21; 930/70; 930/260
[58] Field of Search ...................... 530/306, 324, 530/325; 514/9, 2, 805; 930/21, 70, 260

[56] References Cited

U.S. PATENT DOCUMENTS

| | | | |
|---|---|---|---|
| 3,761,459 | 9/1973 | Pless et al. | 530/324 |
| 5,109,111 | 4/1992 | Rivier et al. | 530/306 |
| 5,235,036 | 10/1993 | Kornreich et al. | 530/324 |
| 5,245,009 | 9/1993 | Kornreich et al. | 530/306 |
| 5,278,146 | 1/1994 | Rivier et al. | 530/324 |

OTHER PUBLICATIONS

Rivier et al., Science, vol. 224, pp. 889–891, (May 25, 1984).
Taché et al., "Role of CRF in Stress–Related Alterations of Gastric and Colonic Motor Function", Annals of the New York Academy of Sciences, vol. 697, pp. 233–243 (1993).

Hernandez et al., "Synthesis and Relative Potencies of New Constrained CRF Antagonists", J. Med. Chem. 1993, 36, pp. 2860–2867.

Primary Examiner—Christina Y. Chan
Assistant Examiner—T. D. Wessendorf
Attorney, Agent, or Firm—Fitch, Even, Tabin & Flannery

[57] ABSTRACT

Disclosed are improved CRF peptide antagonists such as those having the formula: Y-D-Phe-$Xaa_{13}$-Leu-Leu-Arg-$Xaa_{17}$-$Xaa_{18}$-Leu-$Xaa_{20}$-Nle-$Xaa_{22}$-$Xaa_{23}$-$Xaa_{24}$-$Xaa_{25}$-$Xaa_{26}$-Leu-$Xaa_{28}$-$Xaa_{29}$-Gln-$Xaa_{31}$-$Xaa_{32}$-$Xaa_{33}$-$Xaa_{34}$-Arg-$Xaa_{36}$-$Xaa_{37}$-Nle-$Xaa_{39}$-$Xaa_{40}$-$Xaa_{41}$-$NH_2$ wherein Y is Ac or hydrogen; $Xaa_{13}$ is His, Tyr or Glu; $Xaa_{17}$ is CML, Glu, Asn or Lys; $Xaa_{18}$ is Val, Nle or Met; $Xaa_{20}$ is Glu, D-Glu, Aib or D-Ala; $Xaa_{22}$ is Ala, Aib, Thr, Asp or Glu; $Xaa_{23}$ is Arg, Orn, Har or Lys; $Xaa_{24}$ is Ala or Aib; $Xaa_{25}$ is Asp or Glu; $Xaa_{26}$ is Gln, Asn or Lys; $Xaa_{28}$ is Ala or Aib; $Xaa_{29}$ is Gln, Aib or Glu, $Xaa_{31}$ is Ala or Aib; $Xaa_{32}$ is His, Aib, Gly, Tyr or Ala; $Xaa_{33}$ is Ser, Aib, Asn, Leu, Thr or Ala; $Xaa_{34}$ is Asn or Aib; $Xaa_{36}$ is Lys, Orn, Arg, Har or Leu; $Xaa_{37}$ is Leu or Tyr; $Xaa_{39}$ is Glu, Aib or Asp; $Xaa_{40}$ is Ile, Aib, Thr, Glu, Ala, Val, Leu, Nle, Phe, Nva, Gly or Gln; and $Xaa_{41}$ is Ala, Ile, Gly, Val, Leu, Nle, Phe, Nva or Gln, wherein CML may be substituted for Leu. Specific CRF antagonists disclosed include [D-$Phe^{12}$, D-$Ala^{20}$, $Nle^{21,38}$]-rCRF(12-41), [D-$Phe^{12}$, $Nle^{21,38}$, $Aib^{34}$]-rCRF (12-41), [D-$Phe^{12}$, $CML^{17}$, $Nle^{21,38}$]-rCRF(12-41), [D-$Phe^{12}$, $Aib^{20}$, $Nle^{21,38}$]-rCRF(12-41), [D-$Phe^{12}$, $Aib^{29}$, $Nle^{21,38}$]-rCRF(12-41), [D-$Phe^{12}$, $CML^{14}$, $Nle^{21,38}$, $Aib^{24,28,31}$]-rCRF(12-41) and [D-$Phe^{12}$, $CML^{15}$, $Aib^{24,28,31}$]-rCRF(12-41).

4 Claims, No Drawings

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
      ( A ) LENGTH: 41 amino acids
      ( B ) TYPE: amino acid
      ( D ) TOPOLOGY: unknown ( i i ) MOLECULE TYPE: peptide ( x i ) SEQUENCE DESCRIPTION: SEQ ID NO:1:

```
Ser Gln Glu Pro Pro Ile Ser Leu Asp Leu Thr Phe His Leu Leu Arg
 1               5                  10                      15

Glu Val Leu Glu Met Thr Lys Ala Asp Gln Leu Ala Gln Gln Ala His
```

20                          25                          30

Ser  Asn  Arg  Lys  Leu  Leu  Asp  Ile  Ala
                   35                  40

(2) INFORMATION FOR SEQ ID NO:2:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:2:

Ser  Glu  Glu  Pro  Pro  Ile  Ser  Leu  Asp  Leu  Thr  Phe  His  Leu  Leu  Arg
    1                   5                        10                       15

Glu  Val  Leu  Glu  Met  Ala  Arg  Ala  Glu  Gln  Leu  Ala  Gln  Gln  Ala  His
                        20                        25                       30

Ser  Asn  Arg  Lys  Leu  Met  Glu  Ile  Ile
                        35                   40

(2) INFORMATION FOR SEQ ID NO:3:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:3:

Ser  Gln  Glu  Pro  Pro  Ile  Ser  Leu  Asp  Leu  Thr  Phe  His  Leu  Leu  Arg
    1                   5                        10                       15

Glu  Met  Leu  Glu  Met  Ala  Lys  Ala  Glu  Gln  Glu  Ala  Glu  Gln  Ala  Ala
                        20                        25                       30

Leu  Asn  Arg  Leu  Leu  Leu  Glu  Glu  Ala
                        35                   40

(2) INFORMATION FOR SEQ ID NO:4:

(i) SEQUENCE CHARACTERISTICS:
        (A) LENGTH: 41 amino acids
        (B) TYPE: amino acid
        (D) TOPOLOGY: unknown (ii) MOLECULE TYPE: peptide (xi) SEQUENCE DESCRIPTION: SEQ ID NO:4:

Ser  Glu  Glu  Pro  Pro  Ile  Ser  Leu  Asp  Leu  Thr  Phe  His  Leu  Leu  Arg
    1                   5                        10                       15

Glu  Val  Leu  Glu  Met  Ala  Arg  Ala  Glu  Gln  Leu  Ala  Gln  Gln  Ala  His
                        20                        25                       30

Ser  Xaa  Arg  Lys  Leu  Met  Glu  Ile  Ile
                        35                   40

(2) INFORMATION FOR SEQ ID NO:5:

(i) SEQUENCE CHARACTERISTICS:
        (A) LENGTH: 33 amino acids
        (B) TYPE: amino acid
        (D) TOPOLOGY: unknown (ii) MOLECULE TYPE: peptide (xi) SEQUENCE DESCRIPTION: SEQ ID NO:5:

```
Xaa Xaa Xaa Xaa Xaa Leu Leu Arg Xaa Xaa Xaa Xaa Xaa Xaa Xaa
1               5                   10                      15

Xaa Xaa Xaa Xaa Xaa Gln Xaa Xaa Xaa Xaa  Arg Xaa Xaa Xaa Xaa Xaa
              20                  25                   30

Xaa
```

( 2 ) INFORMATION FOR SEQ ID NO:6:

( i ) SEQUENCE CHARACTERISTICS:
        ( A ) LENGTH: 41 amino acids
        ( B ) TYPE: amino acid
        ( D ) TOPOLOGY: unknown ( i i ) MOLECULE TYPE: peptide ( x i ) SEQUENCE DESCRIPTION: SEQ ID NO:6:

```
Xaa Xaa Xaa Xaa Xaa Ile Ser Xaa Xaa Leu Xaa Xaa Xaa Xaa Leu Arg
1               5                   10                      15

Xaa Xaa Xaa Xaa Xaa Xaa Xaa Xaa Xaa Xaa Xaa Xaa Xaa Gln Ala Xaa
              20                  25                   30

Xaa Xaa Arg Xaa Xaa Xaa Xaa Xaa Xaa
         35                  40
```

CRF ANTAGONISTS

This invention was made with Government support under Grant No. DK-26741 awarded by the National Institutes of Health. The Government has certain rights in this invention.

This application is a 371 of PCT/U.S. Ser. No. 92/05101, filed Jun. 12, 1992, which is a continuation-in-part of U.S. Ser. No. 07/715,752, filed Jun. 14, 1991, now U.S. Pat. No. 5,245,009 issued Dec. 14, 1993.

This invention is directed to peptides and to methods for pharmaceutical treatment of mammals using such peptides. More specifically, the invention relates to analogs of the hentetracontapeptide CRF, particularly antagonists thereof, to pharmaceutical compositions containing such CRF analogs and to methods of treatment of mammals using such CRF analogs.

BACKGROUND OF THE INVENTION

Experimental and clinical observations have supported the concept that the hypothalamus plays a key role in the regulation of adenohypophysial corticotropic cells secretory functions. Although over 25 years ago, it was demonstrated that factors present in the hypothalamus would increase the rate of ACTH secretion by the pituitary gland, when incubated in vitro or maintained in an organ culture, a physiologic corticotropin releasing factor (CRF) was not characterized until ovine CRF (oCRF) was characterized in 1981. As disclosed in U.S. Pat. No. 4,415,558, oCRF was found to have the formula (SEQ ID NO:1): Ser-Gln-Glu-Pro-Pro-Ile-Ser-Leu-Asp-Leu-Thr-Phe-His- Leu-Leu-Arg-Glu-Val-Leu-Glu-Met-Thr-Lys-Ala-Asp-Gln- Leu-Ala-Gln-Gln-Ala-His-Ser-Asn-Arg-Lys-Leu-Leu-Asp-Ile-Ala wherein the C-terminus is amidated. oCRF lowers blood pressure in mammals when injected peripherally and stimulates the secretion of ACTH and β-endorphin.

Rat CRF(rCRF) was later isolated, purified and characterized as a hentetracontapeptide having the formula (SEQ ID NO:2): Ser-Glu-Glu-Pro-Pro-Ile-Ser-Leu-Asp-Leu-Thr-Phe-His- Leu-Leu-Arg-Glu-Val-Leu-Glu-Met-Ala-Arg-Ala-Glu-Gln-Leu-Ala- Gln-Gln-Ala-His-Ser-Asn-Arg-Lys-Leu-Met-Glu-Ile-Ile, wherein the C-terminus is amidated, as described in U.S. Pat. No. 4,489,163. It is sometimes referred to as rat amunine. The formula of human CRF has now been determined to be the same as that of rCRF, and the terms rCRF and hCRF are used interchangeably. A CRF analog has been developed having a high alpha-helical forming potential and the formula (SEQ ID NO: 3): Ser-Gln-Glu-Pro-Pro-Ile-Ser-Leu-Asp-Leu-Thr-Phe-His-Leu-Leu-Arg-Glu-Met-Leu-Glu-Met-Ala-Lys-Ala-Glu-Gln-Glu-Ala- Glu-Gln-Ala-Ala-Leu-Asn-Arg-Leu-Leu-Leu-Glu-Glu-Ala, wherein the C-terminus is amidated; it is referred to as AHC (alpha-helical CRF) and is described in U.S. Pat. No. 4,594,329.

Synthetic rCRF, oCRF and AHC stimulate ACTH and β-endorphin-like activities (β-END-LI) in vitro and in vivo and substantially lower blood pressure when injected peripherally. Antagonists of these compounds are disclosed in U.S. Pat. No. 4,605,642, issued Aug. 12, 1986.

SUMMARY OF THE INVENTION

Analogs of these improved biological activity, e.g. CRF peptides have been discovered which exhibit longer lasting biological activity, and certain analogs which are of particular interest are novel CRF antagonists that have improved biological properties in comparison to known CRF antagonists. These peptides preferably have a specific D-isomer substitution in the 20-position or have Aib in certain selected positions, i.e. from position 20 to the C-terminus. The peptide antagonists preferably optionally also have D-Phe in the 12-position and norleucine in the 21 and 38 positions. Other optional substitutions may also be made throughout the molecule as previously taught. For example, a Leu residue in the 17-position and/or the 37-position substituted with a methyl group on its α-carbon atom is considered to enhance biopotency, and other Leu residues throughout the molecule, particularly in the 14- and 15-positions, may also be so substituted and employed in combination with the aforementioned substitutions. Beginning at the N-terminus, the peptide is shortened by the deletion of a sequence of 8 to about 11 residues to produce the antagonists, and it is preferably shortened by deletion of 11 residues. CRF agonists having similar substitutions also have increased biopotency and duration of bioactivity.

Pharmaceutical compositions in accordance with the invention include such CRF analogs, including the antagonists, or nontoxic addition salts thereof, dispersed in a pharmaceutically or veterinarily acceptable liquid or solid carrier. The administration of such peptides or pharmaceutically or veterinarily acceptable addition salts thereof to mammals, particularly humans, in accordance with the invention may be carried out for the regulation of secretion of ACTH, β-endorphin, β-lipotropin, other products of the pro-opiomelanocortin gene and corticosterone and/or for affecting mood, behavioral and gastrointestinal functions and autonomic nervous system activities. CRF agonists may be used for the lowering of blood pressure.

DETAILED DESCRIPTION OF THE PREFERRED EMBODIMENTS

The nomenclature used to define the peptides is that specified by Schroder & Lubke, "The Peptides", Academic Press (1965) wherein, in accordance with conventional representation, the amino group appears to the left and the carboxyl group to the right. The standard 3-letter abbreviations are used to identify the alpha-amino acid residues, and where the amino acid residue has isomeric forms, it is the L-form of the amino acid that is represented unless otherwise expressly indicated, e.g. Ser=L-serine, Orn=L-ornithine, Nle=L-norleucine, Nva=L-norvaline, Abu=L-2-aminobutyric acid, Dbu=L-2,4-diaminobutyric acid, Dpr=L-2,3-diaminopropionic acid, and Har=L-homoarginine. In addition the following abbreviations are used: CML= $C^{\alpha}CH_3$-L-leucine; Aib=$C^{\alpha}CH_3$-L-alanine or 2-aminoisobutyric acid; Nal=L-β-(1- or 2-naphthyl) alanine and Pal=L-β-(2-, 3- or 4-pyridyl) alanine.

A preferred group of antagonists are those having the formula: Y-D-Phe-$Xaa_{13}$-Leu-Leu-Arg-$Xaa_{17}$-$Xaa_{18}$ -Leu-$Xaa_{20}$-Nle-$Xaa_{22}$-$Xaa_{23}$-$Xaa_{24}$-$Xaa_{25}$-$Xaa_{26}$-Leu-$Xaa_{28}$-$Xaa_{29}$ -Gln-$Xaa_{31}$-$Xaa_{32}$-$Xaa_{33}$-$Xaa_{34}$-Arg-$Xaa_{36}$-$Xaa_{37}$-Nle-$Xaa_{39}$-$Xaa_{40}$ -$Xaa_{41}$-$NH_2$ wherein Y is Ac or hydrogen; $Xaa_{13}$ is His, Tyr or Glu; $Xaa_{17}$ is Glu, Asn or Lys; $Xaa_{18}$ is Val, Nle or Met; $Xaa_{20}$ is Glu, D-Glu, Aib or D-Ala; $Xaa_{22}$ is Ala, Aib, Thr, Asp or Glu; $Xaa_{23}$ is Arg, Orn, Har or Lys; $Xaa_{24}$ is Ala or Aib; $Xaa_{25}$ is Asp or Glu; $Xaa_{26}$ is Gln, Asn or Lys; $Xaa_{28}$ is Ala or Aib; $Xaa_{29}$ is Gln, Aib or Glu, $Xaa_{31}$ is Ala or Aib; $Xaa_{32}$ is His, Aib, Gly, Tyr or Ala; $Xaa_{33}$ is Ser, Aib, Asn, Leu, Thr or Ala; $Xaa_{34}$ is Asn or Aib; $Xaa_{36}$ is Lys, Orn, Arg, Har or Leu; $Xaa_{37}$ is Leu or Tyr; $Xaa_{39}$ is Glu, Aib or Asp; $Xaa_{40}$ is Ile, Aib, Thr, Glu, Ala, Val, Leu, Nle, Phe, Nva, Gly or Gln; and $Xaa_{41}$ is Ala, Ile, Gly, Val, Leu, Nle, Phe, Nva or Gln, with the proviso that $Xaa_{20}$ is either D-Ala or Aib or $Xaa_{34}$ is Aib; or a nontoxic addition salt thereof. Analogs of this group which are considered to be particularly biopotent are: [D-Phe$^{12}$, D-Ala$^{20}$, Nle$^{21,38}$]-rCRF(12-41), [D-Phe$^{12}$, Nle$^{21,38}$, Aib$^{34}$]-rCRF(12-41) and [D-Phe$^{12}$, Nle$^{21,38}$, Aib$^{28,34}$]-rCRF(12- 41).

Another preferred group of antagonists are those having the formula: Y-D-Phe-$Xaa_{13}$-$Xaa_{14}$-$Xaa_{15}$-Arg-CML-$Xaa_{18}$-$Xaa_{19}$-$Xaa_{20}$-Nle-$Xaa_{22}$ -$Xaa_{23}$-$Xaa_{24}$-$Xaa_{25}$-$Xaa_{26}$-$Xaa_{27}$-$Xaa_{28}$-$Xaa_{29}$-Gln-$Xaa_{31}$-$Xaa_{32}$-$Xaa_{33}$-$Xaa_{34}$-Arg-$Xaa_{36}$-$Xaa_{37}$-Nle-$Xaa_{39}$-$Xaa_{40}$-$Xaa_{41}$-NH$_2$ wherein Y is Ac or hydrogen; $Xaa_{13}$ is His, Tyr or Glu; $Xaa_{14}$ is CML or Leu; $Xaa_{15}$ is CML or Leu; $Xaa_{18}$ is Val, Nle or Met; $Xaa_{19}$ is CML or Leu; $Xaa_{20}$ is Glu, D-Glu, Aib or D-Ala; $Xaa_{22}$ is Ala, Aib, Thr, Asp or Glu; $Xaa_{23}$ is Arg, Orn, Har or Lys; $Xaa_{24}$ is Ala or Aib; $Xaa_{25}$ is Asp or Glu; $Xaa_{26}$ is Gln, Asn or Lys; $Xaa_{27}$ is CML or Leu; $Xaa_{28}$ is Ala or Aib; $Xaa_{29}$ is Gln, Aib or Glu, $Xaa_{31}$ is Ala or Aib; $Xaa_{32}$ is His, Aib, Gly, Tyr or Ala; $Xaa_{33}$ is Ser, Aib, Asn, Leu, Thr or Ala; $Xaa_{34}$ is Asn or Aib; $Xaa_{36}$ is Lys, Orn, Arg, Har or Leu; $Xaa_{37}$ is CML, Leu or Tyr; $Xaa_{39}$ is Glu, Aib or Asp; $Xaa_{40}$ is Ile, Aib, Thr, Glu, Ala, Val, Leu, Nle, Phe, Nva, Gly or Gln; and $Xaa_{41}$ is Ala, Ile, Gly, Val, Leu, Nle, Phe, Nva or Gln, or a nontoxic addition salt thereof. Analogs of this group which have been found to be particularly biopotent are: [D-Phe$^{12}$, CML$^{17}$, Nle$^{21,38}$, Aib$^{24,28,31}$]-rCRF(12-41), [D-Phe$^{12}$, CML$^{17}$, Nle$^{21,38}$]-rCRF(12-41), and [D-Phe$^{12}$, CML$^{17,37}$, Nle$^{21,38}$]-rCRF(12-41).

Still another preferred group of antagonists are those having the formula: Y-D-Phe-$Xaa_{13}$-$Xaa_{14}$-$Xaa_{15}$ -Arg-$Xaa_{17}$$Xaa_{18}$-Leu-$Xaa_{20}$-Nle-$Xaa_{22}$-$Xaa_{23}$-Aib-$Xaa_{25}$-$Xaa_{26}$ -Leu-Aib-$Xaa_{29}$-Gln-Aib-$Xaa_{32}$-$Xaa_{33}$-$Xaa_{34}$-Arg-$Xaa_{36}$-$Xaa_{37}$-Nle- $Xaa_{39}$-$Xaa_{40}$-$Xaa_{41}$-NH$_2$ wherein Y is Ac or hydrogen; $Xaa_{13}$ is His, Tyr or Glu; $Xaa_{14}$ is Leu or CML; $Xaa_{15}$ is CML or Leu; $Xaa_{17}$ is Glu, CML, Asn or Lys; $Xaa_{18}$ is Val, Nle or Met; $Xaa_{20}$ is Glu, D-Glu, Aib or D-Ala; $Xaa_{22}$ is Ala, Aib, Thr, Asp or Glu; $Xaa_{23}$ is Arg, Orn, Har or Lys; $Xaa_{25}$ is Asp or Glu; $Xaa_{26}$ is Gln, Asn or Lys; $Xaa_{29}$ is Gln, Aib or Glu, $Xaa_{32}$ is His, Aib, Gly, Tyr or Ala; $Xaa_{33}$ is Ser, Aib, Asn, Leu, Thr or Ala; $Xaa_{34}$ is Asn or Aib; $Xaa_{36}$ is Lys, Orn, Arg, Har or Leu; $Xaa_{37}$ is Leu or Tyr; $Xaa_{39}$ is Glu, Aib or Asp; $Xaa_{40}$ is Ile, Aib, Thr, Glu, Ala, Val, Leu, Nle, Phe, Nva, Gly or Gln; and Xaa41 is Ala, Ile, Gly, Val, Leu, Nle, Phe, Nva or Gln, with the proviso that $Xaa_{14}$, $Xaa_{15}$ or $Xaa_{17}$ is CML; or a nontoxic addition salt thereof. Analogs of this group which are considered to be particularly biopotent are:

[D-Phe $^{12}$, CML$^{15}$, Nle$^{21,38}$, Aib$^{24,28,31}$]-rCRF (12-41), [D-Phe$^{12}$, CML$^{14}$, Nle$^{21,38}$, Aib, Aib$^{24,28,31}$]-rCRF(12-41) and [D-Phe$^{12}$, CML$^{17}$, Nle$^{21,38}$, Aib$^{24,28,31}$]-rCRF (12-41).

In a broader sense, the invention provides antagonists of CRF having the following formula (SEQ ID NO: 5): Y-$Xaa_9$-$Xaa_{10}$-$Xaa_{11}$-$Xaa_{12}$-$Xaa_{13}$-Leu-Leu-Arg-$Xaa_{17}$-$Xaa_{18}$-$Xaa_{19}$-$Xaa_{20}$-$Xaa_{21}$-$Xaa_{22}$-$Xaa_{23}$-$Xaa_{24}$-$Xaa_{25}$-$Xaa_{26}$-$Xaa_{27}$-$Xaa_{28}$-$Xaa_{29}$-Gln-$Xaa_{31}$-$Xaa_{32}$-$Xaa_{33}$-$Xaa_{34}$-Arg-$Xaa_{36}$ -$Xaa_{37}$-$Xaa_{38}$-$Xaa_{39}$-$Xaa_{40}$-$Xaa_{41}$-NH$_2$ wherein Y is an acyl group having 7 or less carbon atoms or hydrogen; $Xaa_9$ is $desXaa_9$ or Asp; $Xaa_{10}$ is $desXaa_{10}$ or Leu; $Xaa_{11}$ is $desXaa_{11}$, Thr or Ser; $Xaa_{12}$ is (Q)D-Phe, D-Tyr, D-Leu, D-His, D-Nal, D-Pal, D-Ile, D-Nle, D-Val, D-Met, Phe or Leu; Q is H, 4Cl or 4F; $Xaa_{13}$ is His, Tyr or Glu; $Xaa_{17}$ is CML, Glu, Asn or Lys; $Xaa_{18}$ is Val, Nle or Met; $Xaa_{19}$ and $Xaa_{24}$ are selected from the group consisting of Leu, Ile, Ala, Aib, Gly, Val, Nle, Phe, Asn and Gln; $Xaa_{20}$ is Aib, D-Glu, Glu or D-Ala; $Xaa_{21}$ is Nle, Met, Nva, Ile, Ala, Leu, Val, Phe, Asn or Gln; $Xaa_{22}$ is Ala, Aib, Thr, Asp or Glu; $Xaa_{23}$ is Arg, Orn, Har or Lys; $Xaa_{25}$ is Asp or Glu; $Xaa_{26}$ is Gln, Asn or Lys; $Xaa_{27}$ is Leu, Ile, Ala, Val, Nva, Met, Nle, Phe, Asp, Asn, Gln or Glu; $Xaa_{28}$ is Ala, Aib, Arg or Lys; $Xaa_{29}$ is Gln, Aib or Glu; $Xaa_{31}$ is Ala or Aib; $Xaa_{32}$ is His, Aib, Gly, Tyr or Ala; $Xaa_{33}$ is Ser, Aib, Asn, Leu, Thr or Ala; $Xaa_{34}$ is Aib or Asn; $Xaa_{36}$ is Lys, Orn, Arg, Har or Leu; $Xaa_{37}$ is Leu or Tyr; $Xaa_{38}$ is Nle; $Xaa_{39}$ is Glu, Aib or Asp; $Xaa_{40}$ is Ile, Aib, Thr, Glu, Ala, Val, Leu, Nle, Phe, Nva, Gly or Gln; and $Xaa_{41}$ is Ala, Ile, Gly, Val, Leu, Nle, Phe, Nva or Gln; wherein CML may be substituted for Leu; or a nontoxic addition salt thereof, provided, however, that $Xaa_{20}$ is Aib or D-Ala, or $Xaa_{29}$ or $Xaa_{34}$ is Aib. Antagonists in accordance with this formula exhibit excellent binding to pituitary receptors for native CRF.

In a still broader sense, there are provided analogs of CRF of the following formula (SEQ ID NO: 6): Y-$Xaa_1$-$Xaa_2$-$Xaa_3$-$Xaa_4$-$Xaa_5$-Ile-Ser-$Xaa_8$-$Xaa_9$-Leu-$Xaa_{11}$-$Xaa_{12}$ -$Xaa_{13}$-$Xaa_{14}$-Leu-Arg-$Xaa_{17}$-$Xaa_{18}$-$Xaa_{19}$-$Xaa_{20}$-$Xaa_{21}$-$Xaa_{22}$-$Xaa_{23}$ -$Xaa_{24}$-$Xaa_{25}$-$Xaa_{26}$-$Xaa_{27}$-$Xaa_{28}$-$Xaa_{29}$-Gln-Ala-$Xaa_{32}$-$Xaa_{33}$-$Xaa_{34}$ -Arg-$Xaa_{36}$-$Xaa_{37}$-$Xaa_{38}$-$Xaa_{39}$-$Xaa_{40}$-$Xaa_{41}$-NH$_2$ wherein Y is an acyl group having 7 or fewer carbon atoms or hydrogen; $Xaa_1$ is Ser, D-Ser or $desXaa_1$; $Xaa_2$ is Glu, Gln, pGlu, D-pGlu or $desXaa_2$; $Xaa_3$ is Glu, Gly, D-Tyr or $desXaa_3$; $Xaa_4$ is Pro, D-Pro or $desXaa_4$; $Xaa_5$ is Pro or $desXaa_5$; $Xaa_8$ and $Xaa_{19}$ are selected from the group consisting of Leu, Ile, Ala, Gly, Val, Nle, Phe and Gln; $Xaa_9$ is Asp or Glu; $Xaa_{11}$ is Thr or Ser; $Xaa_{12}$ is Phe, D-Phe, Leu, Ala, Ile, Gly, Val, Nle or Gln; $Xaa_{13}$ is His, Tyr or Glu; $Xaa_{14}$ is Leu or Met; $Xaa_{17}$ is Glu, CML or Lys; $Xaa_{18}$ is Val, Nle or Met; $Xaa_{20}$ is Ala, D-Ala, Aib, D-Glu or Glu; $Xaa_{21}$ is Arg, Met, Nva, Ile, Ala, Leu, Nle, Val, Phe or Gln; $Xaa_{22}$ is Ala, Thr, Asp or Glu; $Xaa_{23}$ is Arg, Orn, Har or Lys; $Xaa_{24}$ is Ala, D-Ala, Met, Leu, Ile, Gly, Val, Nle, Phe and Gln; $Xaa_{25}$ is Glu, Ala or Asp; $Xaa_{26}$ is Gly, Gln, Asn or Lys; $Xaa_{27}$ is Leu, Ile, Ala, Val, Nva, Met, Nle, Phe, Asp, Asn, Gln or Glu; $Xaa_{28}$ is Ala, Arg or Lys; $Xaa_{29}$ is Gln, Ala or Glu; $Xaa_{32}$ is Leu, His, D-His, Gly, Tyr or Ala; $Xaa_{35}$ is Ile, Ser, Asn, Leu, Thr or Ala; $Xaa_{34}$ is Aib or Asn; $Xaa_{36}$ is Asn, Lys, Orn, Arg, Har or Leu; $Xaa_{37}$ is Leu or Tyr; $Xaa_{38}$ is Met, Nle or Leu; $Xaa_{39}$ is Ala, Glu or Asp; $Xaa_{40}$ is Ile, Thr, Glu, Ala, Val, Leu, Nle, Phe, Nva, Gly, Asn or Gln; $Xaa_{41}$ is Ile, Ala, Gly, Val, Leu, Nle, Phe or Gln; wherein CML can be substituted for Leu; provided however that $Xaa_{17}$ is CML, $Xaa_{20}$ is D-Ala, or $Xaa_{20}$, $Xaa_{29}$ or $Xaa_{34}$ is Aib, as well as nontoxic salts thereof.

The peptides are synthesized by a suitable method, such as by exclusively solid-phase techniques, by partial solid-phase techniques, by fragment condensation or by classical solution addition.

Common to chemical syntheses of peptides is the protection of the labile side chain groups of the various amino acid moieties with suitable protecting groups which will prevent a chemical reaction from occurring at that site until the group is ultimately removed. Usually also common is the protection of an alpha-amino group on an amino acid or a fragment while that entity reacts at the carboxyl group, followed by the selective removal of the alpha-amino protecting group to allow subsequent reaction to take place at that location. Accordingly, it is common that, as a step in the synthesis, an intermediate compound is produced which includes each of the amino acid residues located in its desired sequence in the peptide chain with various of these residues having side-chain protecting groups.

For example, chemical synthesis of a peptide analog from one preferred group may include the initial formation of an intermediate of the following formula: $X^1$-D-Phe-$Xaa_{13}$($X^7$ or $X^5$)-Leu-Leu-Arg ($X^3$)-$Xaa_{17}$($X^4$, $X^5$ or $X^6$)-$Xaa_{18}$-Leu-$Xaa_{20}$($X^5$)-Nle-$Xaa_{22}$(X2 or $X^5$)-$Xaa_{23}$($X^3$ or $X^6$)-$Xaa_{24}$-$Xaa_{25}$($X^5$)-$Xaa_{26}$($X^4$ or $X^6$)-Leu-$Xaa_{28}$-$Xaa_{29}$($X^4$ or $X^5$)-

Gln($X^4$)-Xaa$_{31}$-Xaa$_{32}$($X^7$)-Xaa$_{33}$($X^2$ or $X^4$)-Xaa$_{34}$ ($X^4$)-Arg($X^3$)-Xaa$_{36}$($X^3$ or $X^6$)-Xaa$_{37}$($X^7$)-Nle-Xaa$_{39}$($X^5$)-Xaa$_{40}$($X^2$, $X^4$ or $X^5$)-Xaa$_{41}$($X^4$)-$X^9$ wherein: the Xaa-groups are as hereinbefore defined.

$X^1$ is either hydrogen or an alpha-amino protecting group. The alpha-amino protecting groups contemplated by $X^1$ are those known to be useful in the art in the step-wise synthesis of polypeptides. Among the classes of alpha-amino protecting groups covered by $X^1$ are (1) acyl-type protecting groups, such as formyl, acrylyl(Acr), benzoyl(Bz) and acetyl(Ac), which are preferably used only at the N-terminal; (2) aromatic urethan-type protecting groups, such as benzyloxycarbonyl(Z) and substituted Z, such as p-chlorobenzyloxycarbonyl, p-nitrobenzyloxycarbonyl, p-bromobenzyloxycarbonyl, p-methoxybenzyloxycarbonyl; (3) aliphatic urethan protecting groups, such as t-butyloxycarbonyl (BOC), diisopropylmethoxycarbonyl, isopropyloxycarbonyl, ethoxycarbonyl, allyloxycarbonyl; (4) cycloalkyl urethan-type protecting groups, such as fluorenyl methyloxycarbonyl (FMOC), cyclopentyloxy-carbonyl, adamantyloxycarbonyl, and cyclohexyloxy-carbonyl; and (5) thiourethan-type protecting groups, such as phenylthiocarbonyl. The preferred alpha-amino protecting group is BOC.

$X^2$ is a protecting group for the hydroxyl group of Thr and Ser and is preferably selected from the class consisting of acetyl(Ac), benzoyl(Bz), tertbutyl, triphenylmethyl(trityl), tetrahydropyranyl, benzyl ether(Bzl) and 2,6-dichlorobenzyl (DCB). The most preferred protecting group is Bzl. $X^2$ can be hydrogen, which means there is no protecting group on the hydroxyl group.

$X^3$ is a protecting group for the guanidino group of Arg or Har preferably selected from the class consisting of nitro, p-toluenesulfonyl(Tos), Z, adamantyloxycarbonyl and BOC, or is hydrogen. Tos is most preferred.

$X^4$ is hydrogen or a protecting group, preferably xanthyl(Xan), for the amido group of Asn or Gln. Asn or Gln is preferably coupled without side chain protection in the presence of hydroxybenzotriazole (HOBt).

$X^5$ is hydrogen or an ester-forming protecting group for the β- or γ-carboxyl group of Asp or Glu, preferably selected from the esters of cyclohexyl (OChx) benzyl (OBzl), 2,6-dichlorobenzyl, methyl, ethyl and t-butyl (To-Bu). OChx is preferred for a BOC stategy.

$X^6$ is hydrogen or a protecting group for the side chain amino substituent of Lys or Orn. Illustrative of suitable side chain amino-protecting groups are Z, 2-chlorobenzyloxycarbonyl(2-Cl-Z), Tos, t-amyloxycarbonyl(Aoc), BOC and aromatic or aliphatic urethan-type protecting groups as specified hereinbefore. 2-Cl-Z is preferred for a BOC stategy.

When His is present, $X^7$ is hydrogen or a protecting group for the imidazole nitrogen such as Tos or 2,4-dinitrophenyl(DNP), and when Tyr is present, $X^7$ is hydrogen or a protecting group for the hydroxyl group such as DCB. When Met is present, the sulfur may be protected, if desired, with oxygen.

The selection of a side chain amino protecting group is not critical except that it should must be one which is not removed during deprotection of the alpha-amino groups during the synthesis. Hence, the alpha-amino protecting group and the side chain amino protecting group cannot be the same.

$X^9$ is NH$_2$, a protecting group such as an ester or an anchoring bond used in solid phase synthesis for linking to a solid resin support, preferably one represented by the formula: —NH-benzhydrylamine (BHA) resin support and —NH-paramethylbenzhydrylamine (MBHA) resin support. Cleavage from a BHA or MBHA resin directly gives the CRF analog amide. By employing a methyl-derivative of such a resin, a methyl-substituted amide can be created, which is considered to be the equivalent thereof.

In the formula for the intermediate, at least one of $X^1$ $X^2$ $X^3$ $X^4$ $X^5$ $X^6$ and $X^7$ is a protecting group or $X^9$ includes resin support. The particular amino acid chosen for each Xaa-group determines whether there will also be a protecting group attached as specified hereinbefore and as generally known in the art. In selecting a particular side chain protecting group to be used in the synthesis of the peptides, the following rules are followed: (a) the protecting group should be stable to the reagent and under the reaction conditions selected for removing the alpha-amino protecting group at each step of the synthesis, (b) the protecting group should retain its protecting properties and not be split off under coupling conditions and (c) the side chain protecting group must be removable, upon the completion of the synthesis containing the desired amino acid sequence, under reaction conditions that will not alter the peptide chain.

If an acyl group is present at the N-terminus, as represented by Y, acetyl, formyl, acrylyl and benzoyl are preferred.

Thus, in one aspect, there is also provided a process for the manufacture of compounds comprising (a) forming a peptide intermediate, as defined hereinbefore, having at least one protective group wherein: $X^1$, $X^2$, $X^3$, $X^4$, $X^5$, $X^6$ and $X^7$ are each either hydrogen or a protective group, and $X^9$ is either a protective group or an anchoring bond to resin support or NH$_2$ and (b) splitting off the protective group or groups or the anchoring bond from said peptide intermediate and (c) if desired, converting a resulting peptide into a nontoxic addition salt thereof.

When the peptides are prepared by chemical synthesis, they are preferably prepared using solid phase synthesis, such as that described by Merrifield, *J. Am. Chem. Soc.*, 85, p 2149 (1964), although other equivalent chemical syntheses known in the art can also be used as previously mentioned. Solid-phase synthesis is commenced from the C-terminus of the peptide by coupling a protected alpha-amino acid to a suitable resin as generally set forth in U.S. Pat. No. 4,244,946 issued Jan. 21, 1981 to Rivier et al., the disclosure of which is incorporated herein by reference. Such a starting material for an antagonist based upon human CRF can be prepared by attaching alpha-amino-protected Ile to a BHA resin.

Ile protected by BOC is coupled to the BHA resin using methylene chloride and dimethylformamide (DMF). Following the coupling of BOC-Ile to the resin support, the alpha-amino protecting group is removed, as by using trifluoroacetic acid(TFA) in methylene chloride, TFA alone or with HCl in dioxane. Preferably 50 volume % TFA in methylene chloride is used with 0–5 weight % 1,2 ethanedithiol. The deprotection is carried out at a temperature between about 0° C. and room temperature. Other standard cleaving reagents and conditions for removal of specific alpha-amino protecting groups may be used as described in Schroder & Lubke, "The Peptides", 1 pp 72–75 (Academic Press 1965).

After removal of the alpha-amino protecting group of Ile, the remaining alpha-amino- and side chain-protected amino acids are coupled step-wise in the desired order to obtain the intermediate compound defined hereinbefore. As an alternative to adding each amino acid separately in the synthesis, some of them may be coupled to one another prior to addition to the solid phase reactor. The selection of an appropriate coupling reagent is within the skill of the art. Particularly suitable as coupling reagents are N,N'-dicyclohexyl carbodiimide(DCC) and N,N'-diisopropyl carbodiimide(DICI).

Activating or coupling reagents for use in the solid phase synthesis of the peptides are well known in the peptide art. Examples of suitable activating reagents are carbodiimides, such as N,N'-diisopropyl carbodiimide and N-ethyl-N'-(3-dimethylaminopropyl) carbodiimide. Other activating reagents and their use in peptide coupling are described by Schroder & Lubke, supra, in Chapter III and by Kapoor, *J. Phar. Sci.*, 59, pp 1–27 (1970). P-nitrophenyl ester (ONp) can also be used to activate the carboxyl end of Asn or Gln for coupling. For example, BOC-Asn(ONp) can be coupled overnight using one equivalent of HOBt in a 50% mixture of DMF and methylene chloride.

Each protected amino acid or amino acid sequence is introduced into the solid phase reactor in about a fourfold excess, and the coupling is carried out in a medium of dimethylformamide(DMF):$CH_2Cl_2$ (1:1) or in DMF or $CH_2Cl_2$ alone. In instances where the coupling is carried out manually, the success of the coupling reaction at each stage of the synthesis is monitored by the ninhydrin reaction, as described by E. Kaiser et al., *Anal. Biochem.* 34, 595 (1970). In cases where incomplete coupling occurs, the coupling procedure is repeated before removal of the alpha-amino protecting group prior to the coupling of the next amino acid. The coupling reactions can be performed automatically, as on a Beckman 990 automatic synthesizer, using a program such as that reported in Rivier et al., *Biopolymers*, 1978, 17, pp.1927–1938.

After the desired amino acid sequence has been completed, the intermediate peptide is removed from the resin support unless it is desired to first form a cyclizing bond while attached to the resin, as described hereinafter. Removal is effected by treatment with a reagent, such as liquid hydrogen fluoride (HF), which not only cleaves the peptide from the resin but also cleaves all remaining side chain protecting groups $X^2$, $X^3$, $X^4$, $X^5$, $X^6$ and $X^7$ and the alpha-amino protecting group $X^1$, if still present (unless it is an acyl group which is intended to be present in the final peptide), to obtain the peptide. When using hydrogen fluoride for cleaving, anisole or cresole and methylethyl sulfide are included in the reaction vessel as scavengers. When Met is present in the sequence, the BOC protecting group may be cleaved with trifluoroacetic acid(TFA)/ethanedithiol prior to cleaving the peptide from the resin to eliminate S-alkylation.

The following Example sets forth a preferred method for synthesizing CRF antagonists by the solid-phase technique.

EXAMPLE I

The synthesis of [D-Phe[12] CML[17], Nle[21,38]]-human CRF(12–41) having the formula: H-D-Phe-His-Leu-Leu-Arg-CML-Val-Leu-Glu-Nle-Ala-Arg-Ala-Glu-Gln-Leu-Ala- Gln-Gln-Ala-His-Ser-Asn-Arg-Lys-Leu-Nle-Glu-Ile-Ile-$NH_2$ is conducted in a stepwise manner on a MBHA hydrochloride resin, such as available from Bachem, Inc., having a substitution range of about 0.1 to 0.7 mmoles/gm. resin. The synthesis is performed on an automatic Beckman 990B peptide synthesizer using a suitable program, preferably as follows:

| STEP | REAGENTS AND OPERATIONS | MIX TIMES MIN. |
|---|---|---|
| 1 | $CH_2Cl_2$ wash-80 ml. (2 times) | 3 |
| 2 | Methanol(MeOH) wash-30 ml. (2 times) | 3 |
| 3 | $CH_2Cl_2$ wash-80 ml. (3 times) | 3 |
| 4 | 50 percent TFA plus 5 percent 1,2-ethanedithiol in $CH_2Cl_2$-70 ml. (2 times) | 12 |
| 5 | Isopropanol wash-80 ml. (2 times) | 3 |
| 6 | TEA 12.5 percent in $CH_2Cl_2$-70 ml. (2 times) | 5 |
| 7 | MeOH wash-40 ml. (2 times) | 2 |
| 8 | $CH_2Cl_2$ wash-80 ml. (3 times) | 3 |
| 9 | Boc-amino acid (10 mmoles) in 30 ml. of either DMF or $CH_2Cl_2$, depending upon the solubility of the particular protected amino acid, (1 time) plus DCC (10 mmoles) in $CH_2Cl_2$ | 30–300 |

Coupling of BOC-Ile results in the substitution of about 0.35 mmol. Ile per gram of resin. All solvents that are used are carefully degassed, preferably by sparging with an inert gas, e.g. helium or nitrogen.

After deprotection and neutralization, the peptide chain is built step-by-step on the resin. Generally, one to two mmol. of BOC-protected amino acid in methylene chloride is used per gram of resin, plus one equivalent of 2 molar DCC in methylene chloride, for two hours. When BOC-Arg(Tos) is being coupled, a mixture of 50% DMF and methylene chloride is used. Bzl is used as the hydroxyl side-chain protecting group for Ser. BOC-Asn or BOC-Gln is coupled in the presence of one equivalent of DCC and two equivalents of HOBt in a 50% mixture of DMF and methylene chloride. 2-Cl-Z is used as the protecting group for the Lys side chain. Tos is used to protect the guanidino group of Arg and the imidazole group of His, and the side chain carboxyl group of Glu is protected by OChx. At the end of the synthesis, the following composition is obtained: BOC-D-Phe-His(Tos)-Leu-Leu-Arg(Tos)-$C^\alpha CH_3$Leu-Val-Leu- Glu-(OChx)-Nle-Ala-Arg(Tos)-Ala-Glu(OChx)-Gln-Leu-Ala-Gln-Gln-Ala-His(Tos)-Ser(Bzl)-Asn-Arg(Tos)-Lys (2-Cl-Z)-Leu-Nle-Glu(OChx)-Ile-Ile-MBHA resin support.

In order to cleave and deprotect the resulting protected peptide-resin, it is treated with 1.5 ml. anisole, 0.5 ml. of methylethylsulfide and 15 ml. hydrogen fluoride (HF) per gram of peptide-resin, first at −20° C. for 20 min. and then at 0° C. for one and one-half hours. After elimination of the HF under high vacuum, the resin-peptide is washed with dry diethyl ether, and the peptides are then extracted with de-gassed 2N aqueous acetic acid and separated from the resin by filtration.

The cleaved and deprotected peptide is then dissolved in 0–5% acetic acid and subjected to purification which may include Sephadex G-50 fine gel filtration.

The peptide is purified by gel permeation followed by semi-preparative HPLC as described in Rivier et al., *Peptides: Structure and Biological Function* (1979) pp. 125–128, and Rivier et al. *J, Chromatography* (1983). The chromatographic fractions are carefully monitored by HPLC, and only the fractions showing substantial purity are pooled.

Specific optical rotation of the hCRF peptide, which is synthesized and purified in the foregoing manner, is measured on a Perkin Elmer Model 241 Polarimeter as $[\alpha]_D^{22}$= −55° ±1.0 (c=1 in 1% acetic acid) (without correction for the presence of $H_2O$ and TFA); it has a purity of greater than about 95%. Purity is further confirmed by mass spectroscopy (MS) and capillary zone electrophoresis.

To check whether the precise sequence is achieved, the CRF analog is hydrolyzed in sealed evacuated tubes containing 4 molar methane sulfonic acid, 3μl of thioglycol/ml. and 1 nmol of Nle (as an internal standard) for 9 hours at 140° C. Amino acid analysis of the hydrolysates using a Beckman 121 MB amino acid analyzer shows amino acid ratios which confirm that the 30-residue peptide structure has been obtained.

EXAMPLE II

The peptide [D-Phe$^{12}$, D-Ala$^{20}$, Nle$^{21,38}$]-rCRF (12-41) having the formula: H-D-Phe-His-Leu-Leu-Arg- Glu-Val-Leu-D-Ala-Nle-Ala-Arg-Ala-Glu-Gln-Leu-Ala-Gln- Gln-Ala-His-Ser-Asn-Arg-Lys-Leu-Nle-Glu-Ile-Ile-NH$_2$ is synthesized. The peptide is biopotent and inhibits the secretion of ACTH and β-END-LI in response to various stimuli.

Specific optical rotation of the CRF peptide, which is synthesized and purified in the foregoing manner, is measured on a Perkin Elmer Model 241 Polarimeter as $[\alpha]_D^{22}=$ −33° ±1.0 (c=1 in 50% acetic acid) (without correction for the presence of H$_2$O and TFA); it has a purity of greater than about 95%.

Amino acid analysis of the resultant, purified peptide is consistent with the formula for the prepared peptide and confirms that the 30-residue peptide structure is obtained.

EXAMPLE III

The peptide [D-Phe$^{12}$, Nle$^{21,38}$, Aib$^{34}$]-rCRF (12–41) having the formula: H-D-Phe-His-Leu-Leu-Arg- Glu-Val-Leu-Glu-Nle-Ala-Arg-Ala-Glu-Gln-Leu-Ala-Gln- Gln-Ala-His-Ser-Aib-Arg-Lys-Leu-Nle-Glu-Ile-Ile-NH$_2$ is synthesized. The peptide is biopotent and inhibits the secretion of ACTH and β-END-LI in response to various stimuli.

Specific optical rotation of the CRF peptide, which is synthesized and purified in the foregoing manner, is measured on a Perkin Elmer Model 241 Polarimeter as $[\alpha]_D^{22}=$ −23.9° ±1.0 (c=1 in 50% acetic acid) (without correction for the presence of H$_2$O and TFA); it has a purity of greater than about 96%.

The antagonist peptide prepared in Example I is tested using the procedure set forth in detail in J. Rivier et al., Science, 224, 889–891 (1984) to determine its effect in blocking by 50% the secretion of ACTH stimulated by a 1 nM dose of oCRF. Compared to AHC(9–41), a potent CRF antagonist which was disclosed in U.S. Pat. No. 4,605,642, this peptide was about 40 times as potent, i.e. 39.59(20.18–80.21). The specificity of this inhibition is demonstrated by the finding of no effect of the standard antagonist on GRF-stimulated secretion of GH, GnRH-stimulated secretion of LH and FSH or TRF-stimulated secretion of TSH and prolactin. Similar testing shows that the peptide prepared in Example II is more than 3 times as potent as AHC(9–41), and that the peptide prepared in Example III is about 15 times as potent.

The in vivo effect of CRF antagonists is tested on the spontaneous ACTH release by adrenalectomized rats. The iv injection of 3 mg/kg BW (about 2.7 nmole) is considered to cause a marked decrease in plasma ACTH levels (measured as described in Vale et al. Science, 213, 1394, 1981), which is statistically significant. In the intact, non-anesthetized rats, the antagonists are considered to induce a dose-related inhibition of CRF-induced ACTH secretion, which is significant. Moreover, the effect of many of these antagonists is particularly long-lasting, causing such decrease in plasma ACTH levels for over 90 minutes following injection at a level of 0.5 mg per rat.

The administration of CRF antagonists reduces the spontaneous ACTH release observed after removal of the corticosteroid feedback, totally blocks the ACTH secretion caused by CRF, and inhibits most of the stressor-induced ACTH release in intact rats. Such effects are comparable to those previously obtained with an antiserum to CRF which demonstrate the role played by endogenous CRF in regulating ACTH secretion, Rivier, C. et al., Science, 218, 377-9(1982).

Synthetic hCRF has been shown to be a powerful stimulator of secretion of ACTH and β-endorphin-like (β-END-LI) immunoactivities in vivo in several rat preparations. Plasma levels of ACTH and β-END-LI are elevated for at least 5–20 minutes following the intraveneous administration of hCRF to nembutal-anesthesized male rats and to quiescent male or female rats with indwelling intravenous cannulae. In addition, hCRF is found to have a dramatic effect to lower blood pressure in rats and dogs when injected peripherally. These antagonists should counteract such effects.

EXAMPLE IV

The peptide [Aib$^{34}$]-rCRF having the formula (SEQ ID NO:4): Ser-Glu-Glu-Pro-Pro-Ile-Ser-Leu-Asp- Leu-Thr-Phe-His-Leu-Leu-Arg-Glu-Val-Leu-Glu-Met-Ala- Arg-Ala-Glu-Gln-Leu-Ala-Gln-Gln-Ala-His-Ser-Xaa-Arg- Lys-Leu-Met-Glu-Ile-Ile, wherein the C-terminus is amidated and Xaa is Aib, is synthesized using a procedure generally as set forth in Example I. The peptide stimulates the secretion of ACTH and β-END-LI and causes significant lowering of blood pressure when injected peripherally.

EXAMPLE V

Using the procedure as generally set forth in Example I, the following group of 11 CRF antagonist peptides are prepared. The optical rotation of each is measured, and they are reported in the right-hand column herebelow. The measurements are considered to be plus or minus 1 degree (without corrections for the presence of H$_2$O and TFA); measurements are made at c=1 in 1% acetic acid, except for those values marked with an asterisk, which were measured in 50% acetic acid.

| COMPOUND | $[\alpha]_D$ |
|---|---|
| A. [D-Phe$^{12}$, Aib$^{20}$, Nle$^{21,38}$]-rCRF(12–41) | −36.4° |
| B. [D-Phe$^{12}$, Aib$^{22}$, Nle$^{21,38}$]-rCRF(12–41) | −55.0° |
| C. [D-Phe$^{12}$, Aib$^{24}$, Nle$^{21,38}$]-rCRF(12–41) | −57.0° |
| D. [D-Phe$^{12}$, Aib$^{28}$, Nle$^{21,38}$]-rCRF(12–41) | −58.5° |
| E. [D-Phe$^{12}$, Aib$^{29}$, Nle$^{21,38}$]-rCRF(12–41) | −30.8°* |
| F. [D-Phe$^{12}$, Aib$^{31}$, Nle$^{21,38}$]-rCRF(12–41) | −59.0° |
| G. [D-Phe$^{12}$, Aib$^{32}$, Nle$^{21,38}$]-rCRF(12–41) | −26.8°* |
| H. [D-Phe$^{12}$, Aib$^{39}$, Nle$^{21,38}$]-rCRF(12–41) | −27.2°* |
| I. [D-Phe$^{12}$, Aib$^{40}$, Nle$^{21,38}$]-rCRF(12–41) | −28.0°* |
| J. [D-Phe$^{12}$, CML$^{14}$, Aib$^{24,28,31}$, Nle$^{21,38}$]-rCRF (12-41) | −44.0° |
| K. [D-Phe$^{12}$, CML$^{15}$, Aib$^{24,28,31}$, Nle$^{21,38}$]-rCRF (12–41) | −46.0° |

These CRF antagonists are tested in vitro using the test procedure described hereinbefore, and the results are set forth in Table 1 herebelow, relative to AHC(9–41) as a standard. In addition, many of the antagonists are also tested in vivo. All that are tested are found to be active, and durations of relative activities are set forth in the table herebelow.

TABLE 1

| PEPTIDE | IN VITRO | IN VIVO |
|---------|----------|---------|
| A | 3.4 (1.4–8.0) | |
| B | 12.6(6.1–27.3) | Still effective after 90 min. |
| C | 11.3(4.3–33.3) | Very effective for 40 min. |
| D | 16.8(7.5–40.0) | Effective for 1 hour |
| E | 6.1(3.2–12.1) | |
| F | 8.8(2.8–31.5) | Effective for 90 min. |
| G | 9.9(4.8–20.6) | |
| H | 4.7(2.1–11.2) | |
| I | 8.5(3.4–21.9) | |
| J | 2.0(1.7–3.4) | Strongly effective for 90 min. |
| K | 5.4(3.4–10.2) | Strongly effective for 40 min. |

Thus, all these CRF antagonists, Peptides A-K, are shown to exhibit bioactivity for their intended purposes.

EXAMPLE VI

Using the procedure as generally set forth in Example I, the following peptides are also prepared which are CRF antagonists:

[D-Ala$^{20}$]-AHC(9-41)
[Aib$^{34}$]-AHC(12-41)
[D-Ala$^{20}$]-oCRF(10-41)
[D-Phe$^{12}$, CML$^{17}$, Aib$^{20}$, Nle$^{21,38}$]-rCRF(12-41)
[D-Phe$^{12}$, D-Ala$^{20}$]-oCRF(12-41)
[Nle$^{18,21}$, D-Ala$^{20}$]-AHC(10-41)
[D-Phe$^{12}$, D-Ala$^{20}$]-rCRF(12-41)
[D-Phe$^{12}$, Nle$^{21}$, Aib$^{34}$]-oCRF(12-41)
[D-Phe$^{12}$, D-Ala$^{20}$]-AHC(12-41)
[D-Phe$^{12}$, CML$^{17}$, Aib$^{22}$, Nle$^{21,38}$]-rCRF(12-41)
[D-Phe$^{12}$, CML$^{17}$, Aib$^{24}$, Nle$^{21,38}$]-rCRF(12-41)
[D-Phe$^{12}$, CML$^{17}$, Aib$^{28}$, Nle$^{21,38}$]-rCRF(12-41)
[D-Phe$^{12}$, CML$^{17}$, Aib$^{29}$, Nle$^{21,38}$]-rCRF(12-41)
[D-Phe$^{12}$, CML$^{17}$, Aib$^{31}$, Nle$^{21,38}$]-rCRF(12-41)
[D-Phe$^{12}$, CML$^{17}$, Aib$^{32}$, Nle$^{21,38}$]-rCRF(12-41)
[D-Phe$^{12}$, Aib$^{34}$, Nle$^{21,38}$]-rCRF(12-41)
[D-Phe$^{12}$, CML$^{17}$, Aib$^{39}$, Nle$^{21,38}$]-rCRF(12-41)
[D-Phe$^{12}$, CML$^{17}$, Aib$^{40}$, Nle$^{21,38}$]-rCRF(12-41)
Nle$^{18,21}$, D-Ala$^{20}$, D-His$^{32}$]-AHC(11-41)
D-Phe$^{12}$, D-Glu$^{20}$, Aib$^{34}$]-rCRF(12-41)
D-Ala$^{20}$, Nle$^{21,38}$]-rCRF(10-41)
D-Phe$^{12}$, Nle$^{21,38}$, Aib$^{39}$]-oCRF(9-41)

These peptides are biopotent in inhibiting the secretion of ACTH and β-END-LI in response to various stimuli.

EXAMPLE VII

Using the procedure as generally set forth in Example I, the following peptides are also prepared which are CRF antagonists:

[CML$^{17}$]-AHC(12-41)
[CML$^{17}$]-oCRF(10-41)
[D-Phe$^{12}$, CML$^{14}$, Nle$^{21,38}$]-rCRF(12-41)
[D-Phe$^{12}$, CML$^{14}$]-oCRF(12-41)
[Nle$^{18,21}$, CML$^{17}$]-AHC(10-41)
[D-Phe$^{12}$, CML$^{17}$, D-Glu$^{20}$]-rCRF(12-41)
[D-Phe$^{12}$, Nle$^{21}$, CML$^{17,37}$]-oCRF(12-41)
[D-Phe$^{12}$, CML$^{15}$]-AHC(12-41)
[D-Phe$^{12}$, CML$^{15}$, Nle$^{21,38}$]-rCRF(12-41)
[D-Phe$^{12}$, CML$^{17,37}$, Nle$^{21,38}$]-rCRF(12-41)
[Nle$^{18,21}$, CML$^{17,37}$, D-His$^{32}$]-AHC(11-41)
[D-Phe$^{12}$, CML$^{17,37}$, Aib$^{34}$]-rCRF(12-41)
[CML$^{17,37}$, Nle$^{21,38}$]-rCRF(10-41)
[D-Phe$^{12}$, CML$^{19}$]-rCRF(12-41)
[D-Phe$^{12}$, Nle$^{21}$, CML$^{27,37}$]-oCRF(12-41)
[D-phe$^{12}$, CML$^{27}$]-AHC(12-41)
[D-Phe$^{12}$, CML$^{19}$, Nle$^{21,38}$]-rCRF(12-41)
[D-Phe$^{12}$, CML$^{27}$, Nle$^{21,38}$]-rCRF(12-41)
[D-Phe$^{12}$, CML$^{19,37}$, Nle$^{21,38}$]-rCRF(12-41)

These peptides are biopotent in inhibiting the secretion of ACTH and β-END-LI in response to various stimuli.

EXAMPLE VIII

Using the procedure set forth in Example I, the following peptides are also prepared:

[Acetyl-Ser$^1$, D-Phe$^{12}$, D-Ala$^{20}$, Nle$^{21,38}$]-rCRF
[D-Phe$^{12}$, D-Ala$^{20}$]-oCRF
[D-Phe$^{12}$, D-Ala$^{20}$, D-Ala$^{24}$]-rCRF(4-41)
[D-Phe$^{12}$, Nle$^{21}$, Aib$^{34}$]-oCRF
Formyl-Ser$^1$, D-Phe$^{12}$, D-Ala$^{20}$, Nle$^{21,38}$]-rCRF
D-Ala$^{20}$, CML$^{17,37}$]-oCRF
[D-Phe$^{12}$, CML$^{17}$]-rCRF(2-41)
[D-Phe$^{12}$, CML$^{17}$, Nle$^{21,38}$]-rCRF
[D-Ala$^{20}$, Nle$^{21,38}$]-oCRF
[D-His$^{32}$, Aib$^{34}$]-oCRF
[D-Phe$^{12}$, D-Ala$^{20,24}$, D-His$^{32}$]-rCRF(6-41)
[Aib$^{20,29}$, Nle$^{21}$, D-His$^{32}$]-oCRF
[Acrylyl-Glu$^2$, D-Ala$^{20}$, Nle$^{21,38}$, D-His$^{32}$]-rCRF(2-41)
[Nle$^{18,21}$, D-Ala$^{20}$, D-His$^{32}$]-AHC
[D-Pro$^4$, D-Phe$^{12}$, Nle$^{18,21}$, D-Ala$^{20}$]-AHC(4-41)
[D-Tyr$^3$, Nle$^{18}$, Nva$^{21}$, D-Ala$^{20}$]-AHC These peptides are biopotent in stimulating the secretion of ACTH and β-END-LI.

CRF profoundly stimulates the pituitary-adrenalcortical axis, and CRF agonists should be useful to stimulate the functions of this axis in some types of patients with low endogenous glucocorticoid production. For example, CRF agonists should be useful in restoring pituitary-adrenal function in patients having received exogenous glucocorticoid therapy whose pituitary-adrenalcortical functions remain supressed. CRF antagonists should be useful to inhibit the functions of this axis in some types of patients with high ACTH and endogenous glucocorticoid production. For example, CRF antagonists may be useful in regulating pituitary-adrenal function in patients having pituitary Cushings disease or any CRF-sensitive tumor.

Most other regulatory peptides have been found to have effects upon the endocrine system, the central nervous system and upon the gastrointestinal tract. Because ACTH and β-END-LI secretion is the "sine qua non" of mammal's response to stress, it was not surprising that CRF has significant effects on the brain as a mediator of many of the body's stress responses. Accordingly, CRF antagonists delivered to the brain should also find application in modifying the mood, learning and behavior of normal and mentally disordered individuals. Furthermore, CRF antagonists in the brain could ameliorate stress-induced conditions to which endogenous CRF might contribute, including some types of hypertension, infertility, decreased libido, impotency and hyperglycemia. Because peripherally administered CRF antagonists reduce the levels of ACTH, β-END, β-lipotropin, other pro-opiomelanocortin gene products and corticosterone, administration of the antagonists may be used to reduce the effects of all of these substances on the brain to thereby influence memory, mood, pain appreciation, etc., and more specifically, alertness, depression and/or anxiety, as well as to modulate the immune system, gastrointestinal tract and adrenalcortical growth and function.

All CRF-related peptides have been shown to dialate the mesenteric vascular bed. CRF antagonists may also be of use for decreasing blood flow to the gastrointestinal tract of mammals, particularly humans. Also, oCRF influences gastric acid production, and CRF antagonists are expected to also be effective to modulate gastrointestinal functions.

CRF antagonists or the nontoxic addition salts thereof, combined with a pharmaceutically or veterinarily acceptable carrier to form a pharmaceutical composition, may be administered to mammals, including humans, either intravenously, subcutaneously, intramuscularly, percutaneously, e.g. intranasally, intracerebroventricularly or orally. The peptides should be at least about 90% pure and preferably should have a purity of at least about 98%; however, lower purities are effective and may well be used with mammals other than humans. This purity mealns that the intended peptide constitutes the stated weight % of all like peptides and peptide fragments present. Administration to humans may be employed by a physician to inhibit endogenous glucocorticoid production or for possible uses outlined above. The required dosage will vary with the particular condition being treated, with the severity of the condition and with the duration of desired treatment. In order to block the stress-related effects of endogenous CRF within the central nervous system, it may be necessary to deliver the CRF antagonists into the cerebral ventricle or spinal fluid. Alternatively, a means of modifying the antagonists so that they could penetrate the blood-brain barrier should be found.

Such peptides are often administered in the form of pharmaceutically or veterinarily acceptable nontoxic salts, such as acid addition salts or metal complexes, e.g., with zinc, iron, calcium, barium, magnesium, aluminum or the like (which are considered as addition salts for purposes of this application). Illustrative of such acid addition salts are hydrochloride, hydrobromide, sulphate, phosphate, tannate, oxalate, fumarate, gluconate, alginate, maleate, acetate, citrate, benzoate, succinate, malate, ascorbate, tartrate and the like. If the active ingredient is to be administered in tablet form, the tablet may contain a binder, such as tragacanth, corn starch or gelatin; a disintegrating agent, such as alginic acid; and a lubricant, such as magnesium stearate. If administration in liquid form is desired, sweetening and/or flavoring may be used, and intravenous administration in isotonic saline, phosphate buffer solutions or the like may be effected.

The peptides should be administered under the guidance of a physician, and pharmaceutical compositions will usually contain the peptide in conjunction with a conventional, pharmaceutically or veterinarily-acceptable carrier. Usually, the dosage will be from about 0.01 to about 10 milligrams of the peptide per kilogram of the body weight of the host animal. As used herein all temperatures are ° C. and all ratios are by volume. Percentages of liquid materials are also by volume.

Although the invention has been described with regard to its preferred embodiments, which constitute the best mode presently known to the inventors, it should be understood that various changes and modifications as would be obvious to one having the ordinary skill in this art may be made without departing from the scope of the invention which is set forth in the claims appended hereto. For example, substitutions and modifications at other positions in the CRF peptide chain can be made in accordance with present or future developments without detracting from the potency of the antagonists. For instance, instead of the simple amide at the C-terminal, a lower alkyl-substituted amide, e.g. 1–4 carbon atoms, i.e. methylamide, ethylamide, etc, may be incorporated. Such peptides are considered as being within the scope of the invention.

Various features of the invention are emphasized in the claims which follow.

What is claimed is:

1. The CRF antagonist having the formula: D-Phe$^{12}$, Aib$^{22}$, Nle$^{21,38}$-rCRF(12-41) or the formula:
D-Phe$^{12}$, Aib$^{31}$, Nle$^{21,38}$-rCRF(12-41).

2. A CRF antagonist peptide having the formula:
D-Phe$^{12}$, CML$^{17}$, Nle$^{21,38}$-rCRF(12-41).

3. A CRF antagonist peptide having the formula:
D-Phe$^{12}$, Nle$^{21,38}$, Aib$^{34}$-rCRF(12-41) or the formula:
D-Phe$^{12}$, Nle$^{21,38}$, Aib$^{29}$-rCRF(12-41).

4. A CRF antagonist peptide having the formula:
D-Phe$^{12}$, CML$^{15}$, Nle$^{21,38}$, Aib$^{24,28,31}$-rCRF(12-41) or the formula:
D-Phe$^{12}$, CML$^{14}$, Nle$^{21,38}$, Aib$^{24,28,31}$-rCRF(12-41).

\* \* \* \* \*